United States Patent

Marcoll

[11] Patent Number: 6,048,495
[45] Date of Patent: Apr. 11, 2000

[54] DETECTOR TUBE

[75] Inventor: Joachim Marcoll, Lübeck, Germany

[73] Assignee: Dräger Sicherheitstechnik GmbH, Germany

[21] Appl. No.: 09/052,561

[22] Filed: Mar. 31, 1998

[30] Foreign Application Priority Data

Sep. 5, 1997 [DE] Germany .................. 197 38 808

[51] Int. Cl.[7] .............. G01N 21/00; G01N 1/48; G01N 30/96; B01L 3/00; B01L 11/00

[52] U.S. Cl. .............. 422/60; 422/59; 422/102; 422/103; 422/86; 422/87; 422/88

[58] Field of Search .............. 422/102, 83, 86, 422/87, 88, 60, 59

[56] References Cited

U.S. PATENT DOCUMENTS

| | | | |
|---|---|---|---|
| 3,388,975 | 6/1968 | Wallace | 422/103 |
| 3,399,973 | 9/1968 | Grosskopf | 422/102 |
| 4,022,578 | 5/1977 | Kretschmer | 23/254 R |
| 4,066,414 | 1/1978 | Selby | 23/259 |
| 4,077,776 | 3/1978 | Moller et al. | 23/254 |
| 4,159,304 | 6/1979 | Shono | 422/104 |
| 4,389,372 | 6/1983 | Lalin | 422/88 |
| 4,481,297 | 11/1984 | Zucal et al. | 436/181 |
| 4,554,133 | 11/1985 | Leichnitz | 422/87 |
| 4,769,218 | 9/1988 | Leichnitz et al. | 422/86 |
| 4,981,656 | 1/1991 | Leitzke | 422/186.18 |
| 5,004,585 | 4/1991 | Bommer | 422/58 |
| 5,910,289 | 6/1999 | Sagstetter | 422/102 |

FOREIGN PATENT DOCUMENTS

| 932750 | 9/1955 | Germany. |
|---|---|---|
| 43 03 860 A1 | 8/1994 | Germany. |

*Primary Examiner*—Randy Gulakowski
*Assistant Examiner*—Paul J. Lee
*Attorney, Agent, or Firm*—McGlew and Tuttle, P.C.

[57] ABSTRACT

A detector tube with a rod-shaped reagent carrier placed into a transparent tube, which reagent carrier is provided with a detection substance, such that the reagent carrier can be placed into the detector tube in a simple manner and that defined flow conditions become established around the reagent carrier. The cross-sectional contour of the reagent carrier is designed as a polygon in such a way that at least some of the outer edges of the reagent carrier are in contact with the inner side of the tube.

20 Claims, 2 Drawing Sheets

DETECTOR TUBE

FIELD OF THE INVENTION

The present invention pertains to a detector tube having the features of a rodshaped reagent carrier placed into a transparent tube, where the reagent carrier is provided with a detection substance.

BACKGROUND OF THE INVENTION

A detector tube of this type has become known from DE Patent No. 932750. Sticks of a porous sintered material, which are impregnated with the detection reagent, are used as reagent carriers in the prior-art detector tube. The sticks are placed into the tubular glass body of the detector tube such that they are located in the direction of the longitudinal axis of the detector tube. A core, around which the sticks are arranged, is provided within the detector tube to fix the sticks within the detector tube.

The drawback of the prior-art detector tube is that a plurality of sticks impregnated with detection reagent must be introduced into the glass body, and that it is difficult to establish homogeneous flow conditions within the detector tube because of the number of sticks.

SUMMARY AND OBJECTS OF THE INVENTION

The basic object of the present invention is to improve a reagent carrier for a detector tube such that it can be placed into the detector tube in a simple manner and that defined flow conditions become established around the reagent carrier.

This object is accomplished by forming the cross-sectional contour of the reagent carrier as a polygon in such a way that at least some of the outer edges of the reagent carrier are in contact with an inner side of the tube.

The advantage of the present invention is essentially that simple and inexpensive manufacture of the detector tube is made possible by the use of a single reagent carrier with a cross-sectional contour that is dimensioned such that some of the outer edges or all outer edges are in contact with the inner wall of the glass body. Flow channels, through which the gas to be tested flows, are formed between the reagent carrier and the glass body. Especially favorable are uniform cross-sectional contours of the detector tube, in which approximately equal air resistances, which lead to a homogeneous flow through the detector tube, become established in the flow channels. The flow resistance can be adapted to prior-art detector tubes, which are filled with a granular reagent, by selecting the number of flow channels or their flow cross sections.

Star-shaped cross-sectional contours are especially advantageous for the reagent carrier. Preferred cross-sectional contours for the reagent carrier also include an equilateral triangle, a square, or an equilateral pentagon or hexagon.

The detection reagent is preferably applied as a coating to the reagent carrier. Dip-coating, spin coating, the ink jet process or sol-gel processes, as they are known from DE 4303860 A1, are especially suitable coating processes. An especially uniform distribution of the reagent on the reagent carrier is achieved with such coating processes.

The materials suitable for the reagent carrier are glass, ceramic or plastics, e.g., perfluoroethylenepropylene (FEP).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
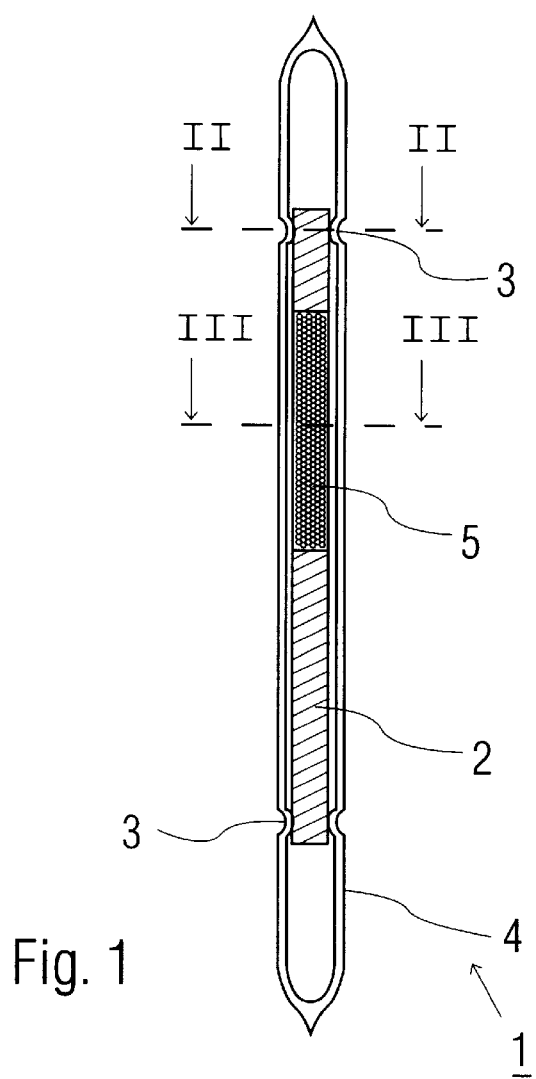
FIG. 1 is a view of the longitudinal section of a detector tube with a reagent carrier

Referring to the drawings, especially FIG. 1, the detector tube 1 and a reagent carrier 2 is held within a glass body 4 by means of individual beads or protrusions 3. The reagent carrier 2 consists of perfluoroethylenepropylene (FEP) and is provided with a reagent layer 5, which was applied according to the ink jet process known from DE 43 03 860 A1. The reagent layer 5 is shown as a dot matrix in FIG. 1.

Figure 2:
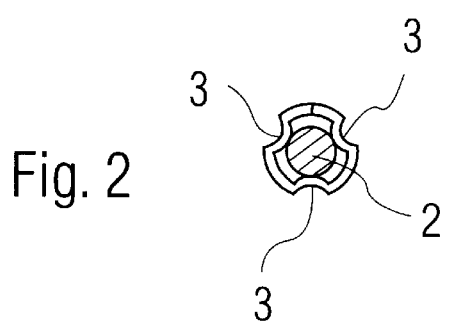
FIG. 2 is a sectional view of the detector tube according to FIG. 1 along the intersecting line II—II.

FIG. 2 shows a sectional view of the detector tube 1 according to FIG. 1 in the area of the beads 3 along the intersecting line II—II. The beads or protrusions 3 touch the reagent carrier 2 at points only in three areas, so that a free flow cross section is still left between the glass tube 4 and the reagent carrier 2.

Figure 3:
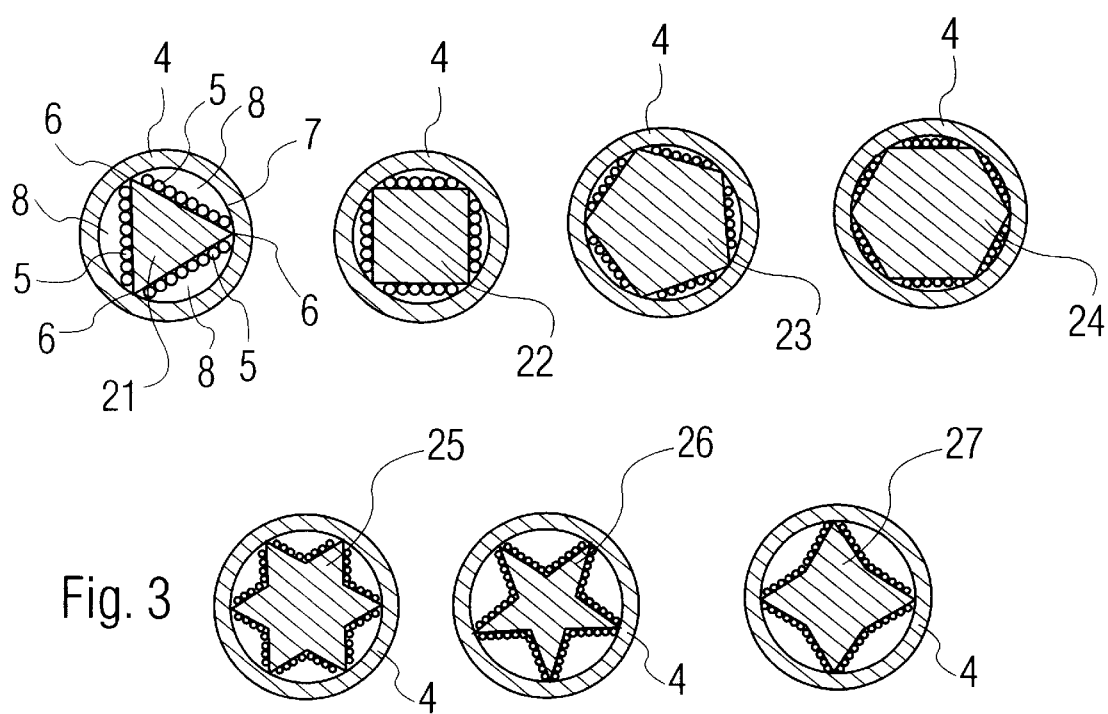
FIG. 3 is a sectional view of the detector tube according to FIG. 1 along the intersecting line III—III with reagent carriers of different designs.

FIG. 3 shows sectional view III—III from FIG. 1 of different designs of reagent carriers of the detector tube 1 according to FIG. 1. Identical components are designated by the same reference numbers as in FIG. 1. Preferred cross-sectional contours of the reagent carrier are an equilateral triangle 21, a square 22, a regular pentagon 23, a hexagon 24, or star-shaped cross sections 25, 26, 27. The reagent carriers 21, 22, 23, 24, 25, 26, and 27 are designed such that their outer edges 6 are in contact with the inner side 7 of the glass tube 4. Only the outer edges 6 of the reagent carrier 21 are provided with reference numbers for the sake of greater clarity. Flow channels 8, through which the air to be tested can reach the reagent layer 5, are formed between the reagent carriers 2, 21, 22, 23, 24, 25, 26, 27 and the glass tube 4. The flow resistance of the detector tube 1 can be changed by valying the cross-sectional contour of the reagent carrier. Thus, detector tubes 1 with the reagent carriers 21, 22, 25, 26, and 27 have a relatively low flow resistance, while it is higher in the case of the reagent carriers 23 and 24.

While specific embodiments of the invention have been shown and described in detail to illustrate the application of the principles of the invention, it will be understood that the invention may be embodied otherwise without departing from such principles.

What is claimed is:

1. A detector tube comprising:
   a transparent tube;
   a rod-shaped reagent carrier placed in said transparent tube, said reagent carrier having a cross-sectional contour shaped as a polygon with planar sides defining outer edges of said reagent carrier, said outer edges being in contact with an inner side of said transparent tube and defining regions of said planar sides spaced from said transparent tube;

a gas detection substance arranged on said planar sides of said reagent carrier, said transparent tube and said planar sides of said reagent carrier with said gas detection substance arranged thereon cooperating to define free flowing gas channels between respective adjacent outer edges.

2. Detector tube in accordance with claim 1, wherein:

said reagent carrier has a star-shaped design.

3. Detector tube in accordance with claim 2, wherein:

said detection substance includes a reagent layer applied to said reagent carrier by one of dip-coating, spin coating, an ink jet process and sol-gel application processes.

4. Detector tube in accordance with claim 2, wherein:

said reagent carrier is formed of one of glass, ceramic and plastic.

5. Detector tube in accordance with claim 1, wherein:

said cross-sectional contour of said reagent carrier is shaped as one of an equilateral triangle, a square, a regular pentagon, and a hexagon.

6. Detector tube in accordance with claim 5, wherein:

said detection substance includes a reagent layer applied to said reagent carrier by one of dip-coating, spin coating, an ink jet process and sol-gel application processes.

7. Detector tube in accordance with claim 5, wherein:

said reagent carrier is formed of one of glass, ceramic and plastic.

8. Detector tube in accordance with claim 1, wherein:

said detection substance includes a reagent layer applied to said reagent carrier by one of dip-coating, spin coating, an ink jet process and sol-gel application processes.

9. Detector tube in accordance with claim 8, wherein:

said reagent carrier is formed of one of glass, ceramic and plastic.

10. Detector tube in accordance with claim 1, wherein:

said reagent carrier is formed of one of glass, ceramic and plastic.

11. Detector tube in accordance with claim 10, wherein:

said plastic is perfluoroethylenepropylene (FEP).

12. The detector tube in accordance with claim 10, wherein each planar side extends uninterrupted from one outer edge to another.

13. The detector tube in accordance with claim 10, wherein each planar side extends from an outer edge inwardly to an inner edge where it joins another planar side.

14. A detector tube comprising:

a transparent tube;

a gas reacting reagent carrier placed in said transparent tube and extending lengthwise within said transparent tube, said reagent carrier having a reagent layer portion with a cross-sectional contour shaped as a polygon with exclusively planar sides defining outer edges of said reagent carrier at an intersection of adjacent planar sides, said outer edges being in contact with an inner side of said transparent tube and defining regions of said planar sides, between adjacent outer edges, spaced from said transparent tube defining free flowing passages with no material therein;

a gas detection substance arranged on said planar sides of said reagent carrier.

15. The detector tube in accordance with claim 14, wherein each planar side extends uninterrupted from one outer edge to another outer edge.

16. The detector tube in accordance with claim 14, wherein each planar side extends from an outer edge inwardly to an inner edge, each inner edge being defined as an intersection of two planar sides, each inner edge being spaced from said transparent tube.

17. A detector tube comprising:

a transparent tube;

a rod-shaped reagent carrier placed in said transparent tube, said reagent carrier having a cross-sectional contour shaped as a polygon with planar sides defining outer edges of said reagent carrier, said outer edges being in contact with an inner side of said transparent tube and defining regions of said planar sides spaced from said transparent tube;

a gas detection substance arranged on said planar sides of said reagent carrier, said transparent tube and said planar sides of said reagent carrier with said gas detection substance arranged thereon cooperating to define free flowing gas channels respectively between adjacent outer edges, each of said free flowing gas channels being a void space free of material and each providing a substantially equal flow resistance wherein homogeneous flow through the detector tube becomes established in the flow channels.

18. The detector tube in accordance with claim 17, wherein each planar side extends uninterrupted from one outer edge to another outer edge.

19. The detector tube in accordance with claim 17, wherein each planar side extends from an outer edge inwardly to an inner edge, each inner edge being defined as an intersection of two planar sides, each inner edge being spaced from said transparent tube.

20. The detector tube in accordance with claim 17, wherein:

said detection substance includes a reagent layer applied to said reagent carrier by one of dip-coating, spin coating, an ink jet process and sol-gel application processes.

* * * * *